(12) United States Patent
Billard et al.

(10) Patent No.: US 7,315,372 B1
(45) Date of Patent: Jan. 1, 2008

(54) INSTRUMENT USING NEAR-FIELD INTENSITY CORRELATION MEASUREMENTS FOR CHARACTERIZING SCATTERING OF LIGHT BY SUSPENSIONS

(75) Inventors: Barton D. Billard, Fredericksburg, VA (US); William Baedke, Norfolk, VA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 183 days.

(21) Appl. No.: 11/251,536

(22) Filed: Sep. 29, 2005

(51) Int. Cl.
*G01N 21/00* (2006.01)

(52) U.S. Cl. .................... 356/338; 356/339; 356/340

(58) Field of Classification Search ........ 356/335–343, 356/315–318, 39–47, 364, 392, 73; 250/573–575, 250/554; 436/63, 72–73
See application file for complete search history.

(56) References Cited

U.S. PATENT DOCUMENTS

| 4,735,504 | A | 4/1988 | Tycko ...................... 356/336 |
| 5,748,311 | A | 5/1998 | Hamann et al. ............ 356/336 |
| 5,818,583 | A | 10/1998 | Sevick-Muraca et al. ... 356/336 |
| 5,851,835 | A * | 12/1998 | Groner ........................ 436/63 |
| 6,630,990 | B2 | 10/2003 | van't Oever et al. ......... 356/39 |
| 6,700,662 | B2 | 3/2004 | Gupta et al. ................ 356/336 |
| 6,778,263 | B2 * | 8/2004 | Ortyn et al. .................. 356/28 |
| 2003/0230709 | A1 * | 12/2003 | Yamada et al. ............. 250/234 |
| 2006/0262301 | A1 * | 11/2006 | Watanabe et al. ........... 356/318 |

FOREIGN PATENT DOCUMENTS

WO    WO 02/103332 A2    12/2002

OTHER PUBLICATIONS

M. Giglio et al.; "Near-field intensity correlations of scattered light", *Applied Optics* 40, 4036-4040, © 2001.
D. Brogioli et al., "Heterodyne near-field scattering", *Applied Physics Letters* 81, 4109-4111, © 2002.
M. Giglio et al., "Space Intensity Correlations in the Near Field of the Scattered Light: A Direct Measurement of the Density Correlation Function g(r)", *Physical Review Letters* 85, 1416-1419, © 1999.
D. Brogioli et al., "A Schlieren method for ultra-low-angle light scattering measurements", *Europhysics Letters* 63, 220-225 © 2003.
M. A. C. Potenza et al., "A novel particle sizing technique based on near field scattering", Proceedings of SPIE 5249, *Optical Design and Engineering*, L. Mazuray et al., eds., 461-470 © Feb. 2004.
M. A. C. Potenza et al., "A new particle sizing technique based on near field scattering", *Nuclear Physics B* (Proceedings Supplements) 150, 34-338, Elsevier © 2005.

* cited by examiner

*Primary Examiner*—Gregory J. Toatley, Jr.
*Assistant Examiner*—Tri Ton
(74) *Attorney, Agent, or Firm*—Gerhard W. Thielman, Esq.; Scott R. Boalick, Esq.

(57) ABSTRACT

Imaging systems may include a light source that directs light towards a scattering medium. A digital imaging system receives transmitted light that is transmitted through the scattering medium substantially without being scattered, and also receives multiple components of scattered light that are passed through the scattering medium after being scattered. The digital imaging system then outputs image intensity information related to the transmitted light and the scattered light. An imaging controller determines a property of the scattering medium, based on spatial correlations related to the image intensity information.

37 Claims, 5 Drawing Sheets

INSTRUMENT USING NEAR-FIELD INTENSITY CORRELATION MEASUREMENTS FOR CHARACTERIZING SCATTERING OF LIGHT BY SUSPENSIONS

STATEMENT OF GOVERNMENT INTEREST

The following description was made in the performance of official duties by employees of the Department of the Navy, and thus the claimed invention may be manufactured, used, licensed by or for the United States Government for governmental purposes without the payment of any royalties thereon.

TECHNICAL FIELD

This description relates to characterization of media scattering properties.

BACKGROUND

Conventional methods exist to determine various media scattering properties, and, in particular, to determine optical properties of scattering media. Scattering media include, for example, fluid media in which particles are distributed or suspended. For example, particles suspended in a fluid may scatter incident light according to a certain angular distribution, and/or may attenuate transmission of the incident light to an identifiable extent. As a result, an intensity distribution or other characteristics of light passing through such a scattering media may be affected, and these effects may be measured and analyzed.

SUMMARY

According to one general aspect, a system includes a light source that is operable to direct light towards a scattering medium. The system also includes a digital imaging system that is operable to receive transmitted light that is transmitted through the scattering medium substantially without being scattered, and to receive interference effects among multiple components of scattered light that are passed through the scattering medium after being scattered thereby, and further operable to output image intensity information resulting from interference among such components. The system also includes an imaging controller that is operable to determine a property of the scattering medium, based on spatial correlations related to the image intensity information.

According to another general aspect, a sequence of images that are formed as a result of source light that has traveled through a scattering medium having particles suspended therein is received, the images containing image intensity information for each of the images. Spatial correlations between intensities of at least two points in each image are determined, and effects of transmitted light that is passed through the scattering medium substantially without scattering are accounted for, based on the spatial correlations. Interference effects of interference among components of scattered light that is scattered by the particles are analyzed, based on the spatial correlations, and a property of the scattering medium is determined, based on the accounting for the effects of transmitted light, the analyzing of the interference effects, and on the spatial correlations.

According to another general aspect, an imaging controller includes an imaging system controller that is operable to determine imaging characteristics of a digital imaging system at which a detecting system detects both scattered light from a light source that has passed through a scattering medium and transmitted light from the light source that has passed through the scattering medium. The imaging controller further includes an image analyzer that is operable to receive image intensity data from the digital imaging system, determine spatial correlations that are associated with the image intensity data, based on interference between components of the scattered light, and further based on the transmitted light, and determine a property of the scattering medium, based on the spatial correlations.

The details of one or more implementations are set forth in the accompanying drawings and the description below. Other features will be apparent from the description and drawings, and from the claims.

DETAILED DESCRIPTION

Figure 1:
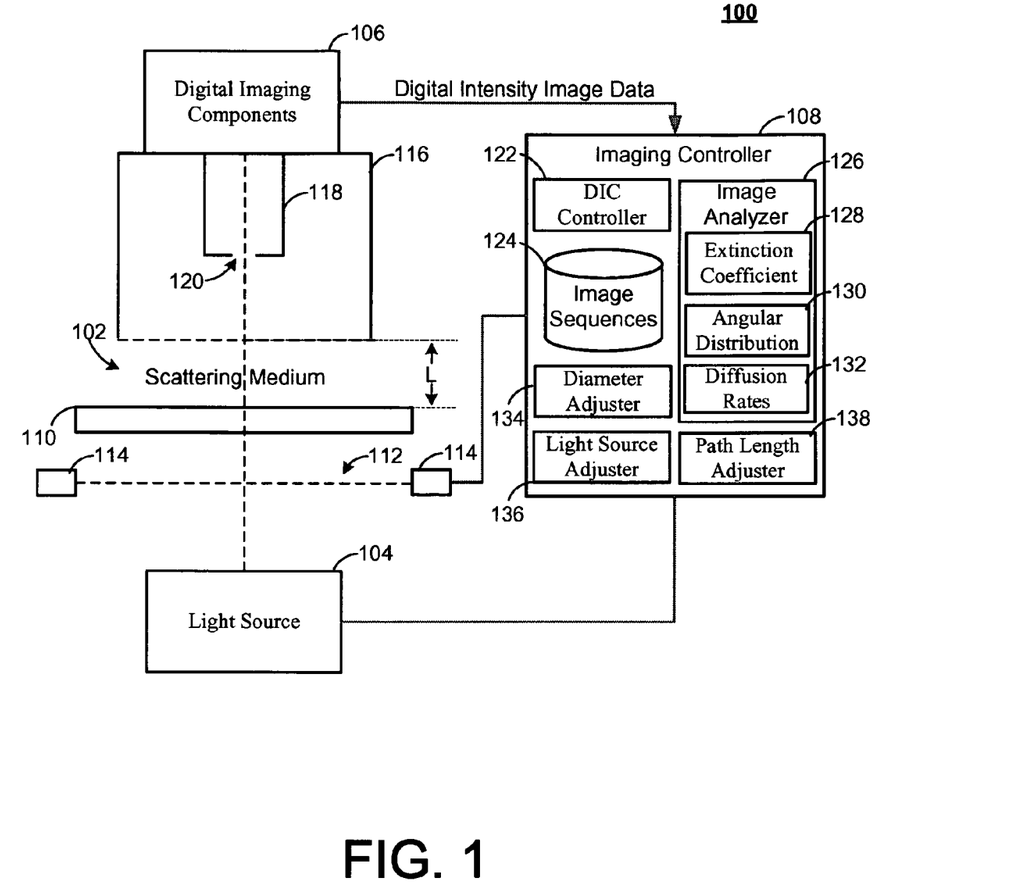
FIG. 1 is a block diagram of an imaging system for determining media scattering properties.

FIG. 1 is a block diagram of an imaging system 100 for determining media scattering properties. In FIG. 1, a scattering medium 102 is placed between a light source 104 and digital imaging components 106. The digital imaging components 106 detect sequences of digital intensity image data over a period of time for output to an imaging controller 108. By analyzing the sequences of digital intensity image data, the imaging controller 108 is able to determine various properties, including scattering and other optical properties, of the scattering medium 102.

As part of such determinations, the imaging controller 108 is operable to remove unwanted components of light received at the digital imaging components 106. For example, some of the light output by the light source 104 may be transmitted through the scattering medium 102 and other elements of the system 100 without being scattered. Such transmitted light may be unnecessary or detrimental to the analysis and characterization of the scattering and other optical properties of the scattering medium 102.

Additionally, some of the light that is output by the light source 104 may be scattered by elements of the system 100 other than the scattering medium 102. Such light may be referred to as stray light, and, like the transmitted light just referenced, may be unnecessary or detrimental to the operation of the system 100.

The imaging controller 108 is operable to account for such unwanted light components as, for example, the transmitted light and the stray light. As a result, the system 100 is operable to analyze a wide range of types of scattering media, and to determine scattering and other optical properties thereof, with a minimal number of components being required by the system 100. That is, for example, the system 100 may not require, but may use in some implementations, physical components for removing the effects of the transmitted light and/or the stray light.

In some implementations, the scattering medium 102 may include a fluid in which certain types of particles are suspended. In such cases, the imaging system 100 may be operable to determine scattering and other optical properties of the scattering medium 102 over a wide range of fluid types and characteristics, and for a variety of types of the suspended particles.

In particular, and as discussed in more detail below, some examples of the scattering medium 102 in which particles are suspended in fluid may be assumed to scatter light from the light source 104 weakly. That is, light from the light source 104 may be assumed to be scattered at most once during its transmission through the scattering medium 102 before passing through to the digital imaging components 106.

Such an assumption may be made, for example, when the scattering medium 102 is "optically thin." For example, the scattering medium 102 may be considered to be optically thin when including a fluid with a relatively low density of scattering particles, or when a path length L of the scattering medium 102 is limited to a certain distance.

In other implementations, such an assumption may not be safely made, e.g., when the scattering medium 102 is considered "optically thick." In these implementations, due to, for example, a relatively large density of suspended particles, or a relatively long path length L, multiple scattering may occur within the scattering medium 102.

That is, light that is incident on, and scattered by, a first particle within the scattering medium 102 may subsequently be incident on, and scattered by a second particle (and, subsequently, a third, fourth, or more particles) within the scattering medium 102. The imaging controller 108 is operable to account for such multiple scattering within the scattering medium 102. As a result, the system 100 is operable to analyze a wide range of such types of scattering media, and to determine scattering and other optical properties thereof.

In the system 100, a window 110 is placed between the scattering medium 102 and the light source 104. An aperture 112 having a diameter D1 is defined by system components 114, such that the light from the light source 104 passes through the aperture 112 prior to being transmitted through the window 110, and, subsequently, through the scattering medium 102.

An assembly 116 is placed on the opposite side of the scattering medium 102 from the window 110, as shown. As described in more detail below, the assembly 116 and the window 110 may be movable relative to one another. As a result, an effective thickness, volume, and/or density of the scattering medium 102 may be determined in a desired manner. Thus, the path length L through the scattering medium 102 may be determined.

Within the assembly 116, a mask 118 may be used to define a near-field region 120. Light from the light source 104 thus passes through the window 110 and the scattering medium 102, and may converge at least in part at the near field region 120 for detection by the digital imaging components 106.

In some implementations, a distance of the near-field region 120 from the scattering medium 102 and/or the light source 104 is such that all desired light that is scattered by the scattering medium 102 is captured by a detector or detector array associated with the digital imaging components. Typically, such capture may be performed without movement of the detector or detector array relative to the scattering medium 102. In these implementations, calibration of multiple detectors or detector arrays relative to one another may not be required, and, similarly, complications resulting from movement of the detector or detectors arrays may be avoided.

The digital imaging components 106 are operable to detect sequences of images, and, more particularly, are operable to detect intensity data with respect to such images. In so doing, operations of the digital imaging components 106 may be controlled by a digital imaging components (DIC) controller 122 within the imaging controller 108. For example, the DIC controller 122 may be operable to determine a number of images within a particular sequence, an exposure time of each image within the sequence, and/or a time interval in between each consecutive pair of images within the sequence. The image sequences, and information about the image sequences, may be stored within an image sequences database or memory 124 within the imaging controller 108.

Then, also within the imaging controller 108, an image analyzer 126 is operable to receive the image data from the memory 124, or directly from the DIC controller 122, and determine various properties of the scattering medium 102, including, for example, properties of particles suspended within the scattering medium 102. For example, the image analyzer 126 may determine an extinction coefficient 128 of the scattering medium 102, an angular distribution 130 of light scattered by the scattering medium 102, or diffusion rates 132 of the suspended particles. These properties are discussed in more detail below, and other properties of the scattering medium 102 also may be determined using the system 100.

In performing the analyses necessary to determine the properties 128, 130, and 132, the image analyzer 126 may use information related to physical or properties of the system 100. For example, a diameter adjuster 134 may be used to change and/or determine a diameter of the aperture 112 (e.g., by adjusting the components 114). A light source adjuster 136 may be used to change and/or determine properties of the light source 104. Also, a path length adjuster 138 may be used to change and/or determine the path length L of the scattering medium. Of course, other adjusters besides the adjusters 134, 136, and 138 may be used, and, moreover, the adjusters 134, 136, and 138 may be partially or wholly located outside of the imaging controller 108.

Figure 2:
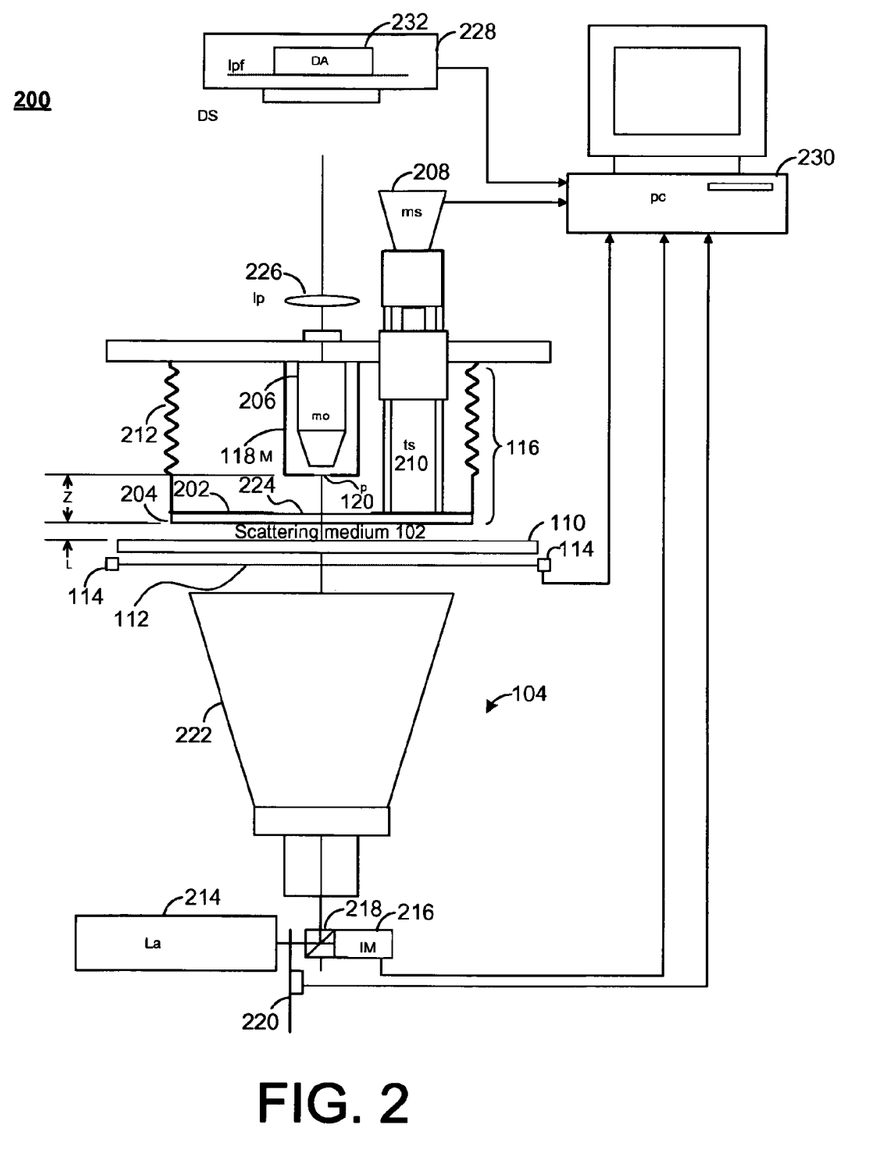
FIG. 2 is a block diagram of an implementation of the imaging system of FIG. 1.

FIG. 2 is a block diagram of an implementation 200 of the imaging system 100 of FIG. 1. In FIG. 2, the sample scattering medium 102 is placed between the window 110, for receiving the illumination beam from the light source 104 as described above, and the assembly 116.

In the implementation of FIG. 2, the assembly 116 includes a light shield 202 with an attached extension window 204. The assembly 116 includes a microscope objective 206, which, in the representation of FIG. 1, is part of the digital imaging components 106.

The sample region, that is, the region containing the scattering medium 102, may be open for sampling ambient scattering media, or may represent a container for holding samples for in vitro measurements. The path length L may be varied as referenced above by a micrometer screw 208, which moves the end of the assembly 116 toward or away from the window 110. The end of the assembly 116 may be attached to a suitable mounting, such as, in the example of FIG. 2, a translation stage 210, which allows the motion toward or away from the window 110. The shield 202 is designed to extend sufficiently, for example, by incorporating a bellows 212, to allow the motion of the end of assembly 116. In some implementations, the shield 202 need not be attached to the extension window 204. The shield 202 may instead be fixed in place as the end of the assembly 116 extends to reduce the path length L in the scattering medium 102, between the window 110 and the extension window 204.

A laser 214 provides illumination as part of the light source 104. An intensity of the laser 214 may be stabilized and/or monitored using an intensity monitor 216. The intensity monitor 216 in FIG. 2 employs a beamsplitter 218, and a detector within the intensity monitor 216.

The illumination intensity of the laser 214 may be adjusted by, for example, a circular linear-wedge neutral-density filter 220. Light from the laser 214 may be spatially filtered, expanded, and collimated with a spatial filter assembly 222 to produce a uniform illumination over the diameter of the aperture 112 in front of the window 110.

In FIG. 2, laser illumination from the laser 214 enters the sample region containing the scattering medium 102, where a portion is transmitted through, and a portion is scattered by, the scattering medium 102. Transmitted laser illumination and scattered light that reaches the extension window 204 in the assembly 116 is transmitted by the extension window 204 toward the microscope objective 206, and at least a portion passes through the planar near-field region 120.

In some implementations, the diameter of the region 120 may be limited to a size of a field of view of the microscope objective 206. The size and shape of the region 120 may further be limited by other components of the imaging system 200, as described in more detail below.

In the implementation of FIG. 2, the microscope objective 206 may be an oil immersion type with an infinity conjugate, so that its front focal plane also is its object plane. A high numerical aperture and high angular aperture may be used to obtain scattered light angular distribution over a large angular range, and to improve the system transfer function. The sine of the angular aperture is equal to the numerical aperture divided by the refractive index of the immersion oil for which the objective is designed.

Immersion oil may be used to fill the volume within assembly 116 between the extension window 204 to the microscope objective 206. In some implementations, a material for the extension window 204 may be a glass that matches the refractive index of the immersion oil for which the objective 206 is designed. In these cases, the angular aperture within the extension window 204 may therefore be the same as the angular aperture of the microscope objective 206.

In some implementations, a diameter of an aperture 224 in the shield 202 where the extension window 204 may attach may be one sufficient to allow full illumination of the numerical aperture of the microscope objective 206 over the region 120. In some implementations, a diameter of the aperture 112 may be at least as large as needed to provide full illumination of the numerical aperture of the microscope objective 206 when the refractive index of the scattering medium matches the refractive index of the immersion oil.

If the diameter of the aperture 112 is at least this large, then the range of measurement may only be limited by the angular aperture of the microscope objective 206. However, for scattering media 102 with a smaller refractive index, a larger angular range of measurement may be possible, if, for example, the diameter of the aperture 112 is larger. For example, if the diameter of the aperture 112 is large enough, the numerical aperture of the microscope objective 206 divided by the refractive index of the scattering medium 102 is the sine of the maximum scattering angle that can be measured.

In other implementations, where the diameter of the aperture 112 is not as large, e.g., if the refractive index of the scattering medium 102 is equal to or smaller than the numerical aperture of the microscope objective 206, then the maximum angular range of measurement of the scattered light distribution may be smaller. The maximum angular range of measurement of the scattered light distribution may be, for example, from 0 degrees (forward scattering) to at least the arctangent of the difference between the diameters of the apertures 112 and of the near-field region 120, divided by twice the sum of the path length L and the illustrated distance Z, as shown in Eq. (1):

$$\theta_{max} = \arctan[(D1-Dp)/2(L+Z)] \qquad \text{Eq. (1)}$$

In Eq. (1), D1 is the diameter of the aperture 112, Dp is the diameter of the region 120, and Z is the distance between this region and the far surface of the extension window 204. As L decreases and Z increases, the actual angular range may become larger.

The diameter D1 of the aperture 112 may be changed in a repeatable manner to facilitate measurement of the extinction coefficient 128. For example, the collimation lens of the spatial filter assembly 222 may be a zoom lens capable of adjusting a size of the illumination beam of the laser 214 in proportion to the chosen diameter D1 of the aperture 112, thereby maintaining efficient illumination of the aperture. When the diameter D1 of the aperture 112 is set at a minimum slightly larger than the diameter Dp of the region 120, the intensity of scattered light reaching the region 120 may be reduced without changing an intensity of the transmitted light that reaches the region 120 without scattering, as referenced above.

The ability to modify the diameter D1 of the aperture 112 (e.g., using the diameter adjuster 134) allows improved discrimination between the effects of the scattered light and the transmitted light, and also allows the laser intensity to be increased. Both effects may be useful, for example, in measuring the transmitted intensity as the optical thickness of the scattering medium 102 increases (so that the transmission consequently decreases). Thus, the aperture 112 may be set to the diameter D1 when measuring the angular distribution of scattered light and particle diffusion rates, and reduced to the minimum diameter, as needed, to aid in extinction coefficient measurement.

When measuring scattering angular distribution with the aperture 112 set to the diameter D1, some additional scattered light may enter through the extension window 204 in a direction that does not take the scattered light through the region 120. Such light may be considered unwanted noise, and the mask 118 prevents the unwanted light from reaching the microscope objective 206 either directly or after reflecting one or more times from the surfaces of the extension window 204 or other parts of the shield 202. In some implementations, the mask 118 may be placed around the region 120 in the front focal plane of the microscope objective 206. Light entering the extension window 204 that misses the region 120 is intercepted directly by the mask 118, and light that passes through the region 120 at an angle too large to be accepted by the microscope objective 206 either is absorbed by the objective 206 or reflected back into the mask 118.

Further in FIG. 2, a positive lens 226 and a digital imaging system 228 connected to a computer 230, where the computer 230 may implement some or all of the imaging controller 108. In some implementations, the lens 226 may be a part of the digital imaging system 228, or, in the context of FIG. 1, may be a part of the digital imaging components 106.

A distance of the lens 226 behind the microscopic objective 206 may be flexible. For example, when an infinite conjugate objective is used, this distance need only be small enough that the light arriving at the lens 226 from the objective 206 can pass through an aperture that is small enough to make aberrations insignificant for the purposes of measurement. The digital imaging system 228 may include a detector or detector array 232 positioned at a focal plane of the lens 226. The lens 226 and the detector array 232 may be centered so that their respective optical axes correspond to that of the objective 206.

In FIG. 2, the infinity conjugate microscope objective 206 accepts and collimates light from the region 120, and the lens 226 focuses that light on the detector array 232, forming an image of the region 120 on the detector array 232. In some implementations, the image may fill the detector array 232. The choice of the focal length of the lens 226 may allow such implementations to be realized, based on a size of the detector array 232 and an angular field of view of the microscope objective 206.

The largest dimension of the detector array 232 (for example, the diagonal) divided by the focal length may be equal to twice the tangent of the angle from the center to the edge of the field. For example, if a specification of the microscope objective 206 provides a field number and designed tube lens focal length of the objective 206, then twice the tangent of the angle from the center to the edge of the field is equal to the field number in millimeters divided by the focal length in millimeters of the tube lens for which the objective 206 is designed.

In some implementations, though, an exact match may not be used. In these implementations, then the focal length of the lens 226 may be larger, or the size of the detector array 232 may be smaller, and a somewhat smaller portion of the region 120 may be used. In these implementations, the region 120 may be regarded as the image of the detector array 232 made by the lens 226 and the microscope objective 206. The magnification may be given by the ratio of the microscope objective 206 focal length divided by the lens 226 focal length. Therefore, the diameter of the aperture 224 in the shield 202, and the size of opening in the mask 118, may be adjusted to accommodate actual dimensions of the region 120.

Continuing the example in which the objective 206 is an infinity conjugate objective, the resolution of the detector array 232 may be given by a minimum pixel spacing equal to a wavelength in air of the laser 214, divide by four times the numerical aperture of the microscope objective 206, and multiplied by the ratio of the foal length of lens 226 to the focal length of the microscope objective 206. For example, a green He-Ne laser has a wavelength in air of 0.5435 micrometers. If the numerical aperture of the microscopic objective is 1.20, and a focal length of the microscopic objective is 3.6 millimeters, then a lens 226 focal length of 210 millimeters would produce a minimum pixel spacing of 6.61 micrometers. In other implementations, a larger pixel spacing may be used.

The computer 230 may be connected to the intensity monitor 216 to receive a readout of the setting of the circular linear-wedge neutral-density filter 220, the path length L, and the diameter D1 of the aperture 112. The computer 230 also may be used to control the acquisition of images by the digital imaging system 228, as described above, including, for example, an exposure time of individual images and/or time between images, and also may be operable to store and analyze the sequences of images taken, as illustrated above with respect to FIG. 1 and described in more detail, below.

Figure 3:
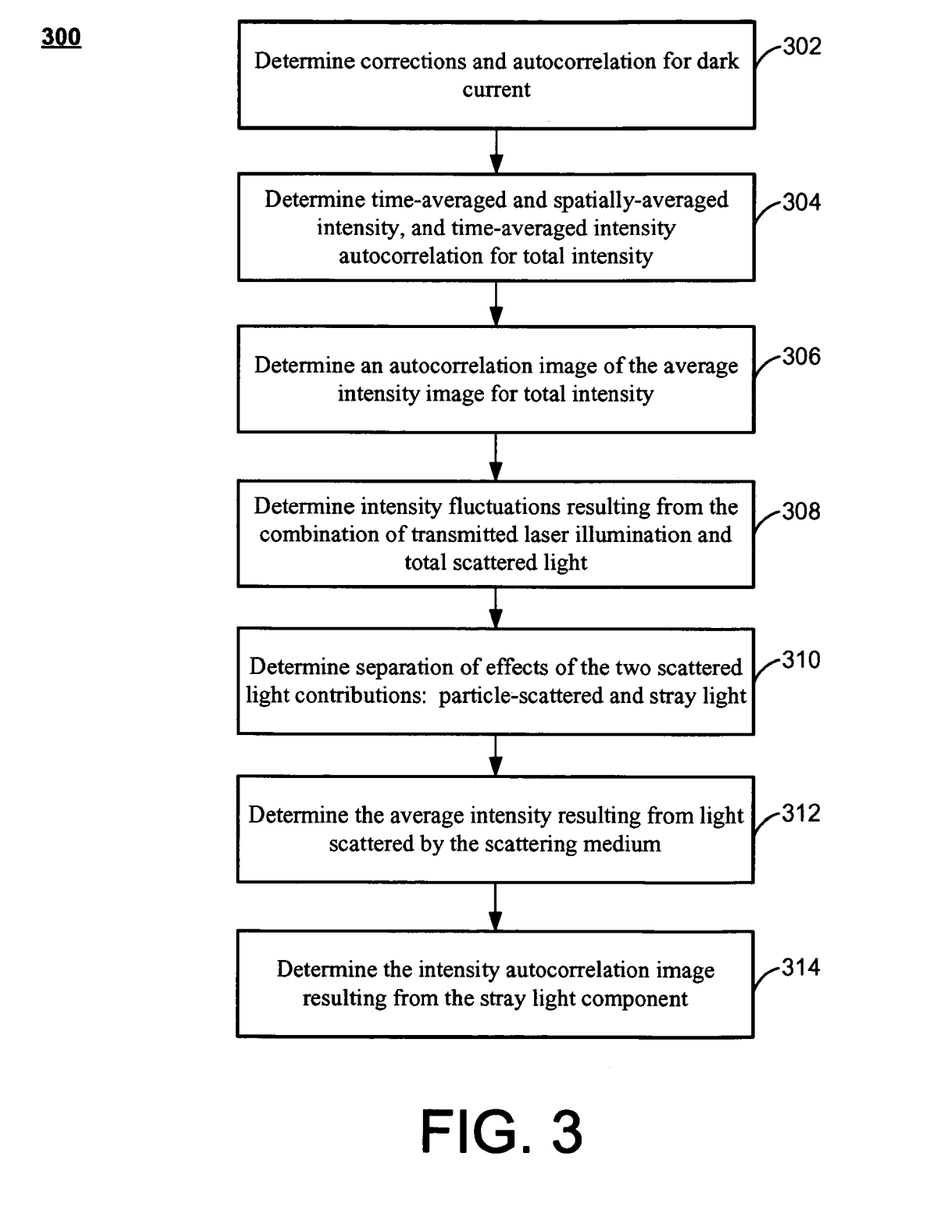
FIG. 3 is a flowchart illustrating processes associated with an operation of the systems of FIGS. 1 or 2.

FIG. 3 is a flowchart illustrating processes associated with an operation of the system 100 or the system 200, or one or more of the other variations thereof just described, or other implementations described in more detail, below. In FIG. 3 and in the following equations, the resulting data to be analyzed includes sequences of digital intensity image data of the form $I(m_x, m_y; j)$, representing the intensity value recorded at position $(x(m_x), y(m_y))=(m_x \Delta x, m_y \Delta y)$ and time $t_j = j \Delta t$, with $m_x$ and $m_y$ being integer column and row numbers of the pixel position, and j being the number of the image in the time sequence.

The parameters $\Delta x$, $\Delta y$ are the effective pixel spacing in the x and y directions (e.g., the pixel spacing in the x and y directions of the detector array 232 divided by the ratio of the focal length of lens 226 to the focal length of the microscope objective 206), and the parameter $\Delta t$ represents the time interval between successive sample images. In the following equations, spatial averaging is indicated by enclosing the quantity averaged in angle brackets ($\langle \; \rangle$), and time averaging is indicated by overbars.

Thus, an average intensity image obtained by averaging of a sequence of images at each pixel may be shown as in Eq. (2):

$$\overline{I(m_x, m_y)} = \overline{I(m_x, m_y; j)} \qquad \text{Eq. (2)}$$

and the average over all pixels of the time-average image may be shown as in Eq. (3):

$$\langle \overline{I} \rangle = \langle \overline{I(m_x, m_y; j)} \rangle \qquad \text{Eq. (3)}$$

An autocorrelation image sequence may be expressed as a sequence of spatial averages of the products of intensity at pixel (m, n) multiplied by the intensity at the shifted pixel $(m+\Delta m, n+\Delta n)$, if the autocorrelation of an image is dependent only on the shift $(\Delta m, \Delta n)$. An example of such an autocorrelation image sequence is shown in Eq. (4):

$$R_I(\Delta m_x, \Delta m_y; j) \equiv \langle I(m_x, m_y; j) I(m_x+\Delta m_x, m_y+\Delta m_y; j) \rangle \qquad \text{Eq. (4)}$$

If needed, corrections for dark current can be obtained (302) from a sequence of intensity images, D(m, n; j), measured with no laser illumination, as shown in Eqs. (5) and (6):

$$\langle \overline{D} \rangle = \langle \overline{D(m_x, m_y; j)} \rangle \qquad \text{Eq. (5)}$$

$$\overline{R_D(\Delta m_x, \Delta m_y)} = \langle \overline{D(m_x, m_y; j) D(m_x+\Delta m_x, m_y+\Delta m_y; j)} \rangle. \qquad \text{Eq. (6)}$$

A sequence of intensity images may be used to calculate a time-averaged intensity image, the spatial average of the time-averaged intensity image, and a time-averaged correlation image (304), as shown in Eqs. (7), (8), and (9), respectively:

$$\overline{I_{\text{raw}}}(m_x, m_y) = \overline{I_{\text{raw}}(m_x, m_y; j)} \qquad \text{Eq. (7)}$$

$$\langle \overline{I_{\text{raw}}} \rangle = \langle \overline{I_{\text{raw}}(m_x, m_y; j)} \rangle \qquad \text{Eq. (8)}$$

$$\overline{R_{I_{\text{raw}}}(\Delta m_x, \Delta m_y)} = \langle \overline{I_{\text{raw}}(m_x, m_y; j) I_{\text{raw}}(m_x+\Delta m_x, m_y+\Delta m_y; j)} \rangle \qquad \text{Eq. (9)}$$

In Eqs. (6) and (9), the intensity autocorrelation image sequence is calculated first, and then the sequence is averaged to produce the time average of the individual intensity autocorrelation images. Conversely, an autocorrelation image of the average intensity image of Eq. (7) may be computed (306) as shown in Eq. (10):

$$R_{\overline{I_{raw}}}(\Delta m_x, \Delta m_y) = \langle \overline{I_{raw}}(m_x, m_y)\overline{I_{raw}}(m_x+\Delta m_x, m_y+\Delta m_y)\rangle \qquad \text{Eq. (10)}$$

The equations for using the dark current corrections are shown in Eqs. (11), (12), and (13):

$$\langle \overline{I}\rangle = \langle \overline{I_{raw}}\rangle - \langle \overline{D}\rangle \qquad \text{Eq. (11)}$$

$$\overline{R_I(\Delta m_x,\Delta m_y)} = \overline{R_{I_{mraw}}(\Delta m_x,\Delta m_y)} - \overline{R_D(\Delta m_x,\Delta m_y)} - 2\langle \overline{I}\rangle\langle \overline{D}\rangle \qquad \text{Eq. (12)}$$

$$R_{\overline{I}}(\Delta m_x, \Delta m_y) = R_{\overline{I_{raw}}}(\Delta m_x, \Delta m_y) - \langle \overline{D}\rangle^2 - 2\langle \overline{I}\rangle\langle \overline{D}\rangle \qquad \text{Eq. (13)}$$

In the above, Eqs. 11 and 12 provide information about the intensity fluctuations resulting from the combination of transmitted laser illumination and total scattered light falling on the region 120 (308). As described, the total scattered light includes light scattered by the scattering medium 102 in the volume between the window 110 and the assembly 116, and the stray light scattered by imperfections in the rest of the instrument. When the fluctuations resulting from the light scattered by the medium are uncorrelated in amplitude and phase from one image to the next, this decorrelation can allow separation of the effects of the two scattered light contributions (310). In this case, Eq. (13) may provide an estimate of the unchanging contribution to the fluctuations that result from the stray light.

The contributions of the scattered light of interest and the stray light may be separated using different techniques. For example, an estimate of the average intensity $\langle \overline{B}\rangle$ resulting from the total scattered light that passes through the region 120 to the microscope objective 206 and recorded may be written as in Eq. (14):

$$\langle \overline{B}\rangle = \langle \overline{I}(m_x, m_y)^2 - [2\overline{I}(m_x,m_y)^2 - R_{\overline{I}}(0,0)]^{1/2}\rangle \qquad \text{Eq. (14)}$$

An estimate of the intensity A of the transmitted laser illumination that passes without scattering may be written as in Eq. (15):

$$A = \langle \overline{I}\rangle - \langle \overline{B}\rangle \qquad \text{Eq. (15)}$$

An estimate of the average intensity $\langle \overline{N}\rangle$ resulting from the stray light component of the total scattered light may be written as in Eq. (16):

$$\langle \overline{N}\rangle = \langle \overline{I}(m_x, m_y)^2 - [2\overline{I}(m_x, m_y)^2 - R_{\overline{I}}(0,0)]^{1/2}\rangle \qquad \text{Eq. (16)}$$

As a result, an estimate of the average intensity $\langle \overline{S}\rangle$ resulting from light scattered by the scattering medium 102 and recorded may be written as in Eq. (17) (312):

$$\langle \overline{S}\rangle = \langle \overline{B}\rangle - \langle \overline{N}\rangle \qquad \text{Eq. (17)}$$

An estimate of the intensity autocorrelation image resulting from the stray light component may be written as in Eq. (18) (314):

$$R_N(\Delta m_x, \Delta m_y) = \qquad \text{Eq. (18)}$$
$$R_{\overline{I-S}}(\Delta m_x, \Delta m_y) = R_{\overline{I}}(\Delta m_x, \Delta m_y) + \langle \overline{S}\rangle^2 - 2\langle \overline{S}\rangle\langle \overline{I}\rangle$$

With the above results for intensity fluctuation statistics, various scattering properties may be calculated. For example, the transmitted laser illumination intensity A is related to the incident intensity $A_0$, the extinction coefficient $\xi$, and the path length L through the sample by the Bouguer-Lambert-Beer law, as shown in Eq. (19):

$$A = A_0 e^{-\xi L} \qquad \text{Eq. (19)}$$

As described above, the systems 100 and/or 200 of FIGS. 1 and/or 2 provide for determination of the path length L. A calibration to determine $A_0$, or a set of measurements of A(L) as a function of varying path lengths L with the illumination kept constant (or adjusted for drift of the laser intensity as monitored by the intensity monitor IM) allows for the solution of Equation 19 for the extinction coefficient $\xi$.

Angular scattering properties of the scattering medium 102 may be obtained from the Fourier transformation of the amplitude autocorrelation function, $J_s(\Delta m_x, \Delta m_y)$, which is given by Eq. (20):

$$J_s(\Delta m_x, \Delta m_y) = \sqrt{R_I(\Delta m_x,\Delta m_y) - \langle \overline{B}\rangle^2} - \sqrt{R_N(\Delta m_x,\Delta m_y) - \langle \overline{N}\rangle^2} \qquad \text{Eq. (20)}$$

The right-hand side of Eq. (20) is the difference between $J_b(\Delta m_x, \Delta m_y)$, the total scattered light amplitude autocorrelation function, and $J_n(\Delta m_x, \Delta m_y)$, the stray light amplitude autocorrelation function, given respectively by Eqs. (21) and (22):

$$J_b(\Delta m_x, \Delta m_y) = \sqrt{R_I(\Delta m_x,\Delta m_y) - \langle \overline{B}\rangle^2} - A \qquad \text{Eq. (21)}$$

$$J_n(\Delta m_x, \Delta m_y) = \sqrt{R_N(\Delta m_x,\Delta m_y) - \langle \overline{N}\rangle^2} - A \qquad \text{Eq. (22)}$$

Computation of the angular distribution of scattered light from an amplitude correlation function estimate is illustrated below for the case of the sample scattered light amplitude correlation function obtained from Eq. (20). The stray light angular distribution computation is analogous.

To compute the angular distribution of scattered light from the amplitude correlation function(s), the spatial frequency distribution $\sigma(q_x, q_y)$, of the scattered light component from the volume of the scattering medium 102 may be calculated using a two-dimensional discrete Fourier transformation, illustrated in Eq. (23):

$$\sigma(q_x, q_y) = \text{Re}\left[\sum_{\Delta m_x=0}^{M_x-1} \sum_{\Delta m_y=0}^{M_y-1} J_s(\Delta m_x, \Delta m_y) e^{\frac{2\pi i(\Delta m_x v_x + \Delta m_y v_y)}{M_x M_y}}\right] \qquad \text{Eq. (23)}$$

In Eq. (23), the function Re[ ] represents the real part of the argument, while $M_x$ and $M_y$ are the respective maximum values of the integer shifts $\Delta m_x$ and $\Delta m_y$, $v_x$ is an integer between $-M_x/2$ and $M_x/2$, $v_y$ is an integer between $-M_y/2$ and $M_y/2$, i is the square root of $-1$, and e is the base of the natural logarithms. On the left-hand side of Eq. (23), the discrete spatial frequency components $q_x$ and $q_y$ are given by Eqs. (24) and (25), respectively:

$$q_x = \frac{2\pi v_x}{M_x \Delta x} \equiv v_x \Delta q_x \qquad \text{Eq. (24)}$$

$$q_y = \frac{2\pi v_y}{M_y \Delta y} \equiv v_y \Delta q_y \qquad \text{Eq. (25)}$$

Eqs. (24) and (25) also define the spacing in spatial frequency, $\Delta q_x$ and $\Delta q_y$, of the points $(q_x, q_y)$. The function $\sigma(q_x, q_y)$ can be corrected for the modulation transfer function of the microscope objective 206, or for the overall system transfer function of the imaging system 100 and/or 200, or variations thereof, obtained by a suitable calibration procedure using Eq. (26):

$$\sigma_c(q_x, q_y) = \frac{\sigma(q_x, q_y)}{MTF(q_x, q_y)} \quad \text{Eq. (26)}$$

In Eq. (26), $\sigma_c(q_x, q_y)$ is the corrected function, and $MTF(q_x, q_y)$ is a modulation transfer function of the microscope objective 206. As just referenced, an overall instrument function can be substituted for the modulation transfer function in Eq. (26), if such a function has been determined by suitable calibration.

The relationship between points $(q_x, q_y)$ in spatial frequency and angular scattering variables $(\theta, \phi)$ is given by Eqs. (27) and (28), respectively:

$$\theta = \arcsin\left[\frac{(q_x^2 + q_y^2)^{1/2}}{n_m k_0}\right] \quad \text{Eq. (27)}$$

$$\varphi = \arctan\left(\frac{q_x}{q_y}\right) - \varphi_0 \quad \text{Eq. (28)}$$

In Eq. (28), $\phi_0$ represents the angle between the desired reference azimuth and the detector array axis chosen as the x direction. In some implementations, it may be assumed that scattering by the scattering medium 102 is symmetric with respect to a change of $\phi$ by $\pi$ radians.

For diffusion rate calculations, it may be convenient to express the scattering distribution as a function of the momentum transfer wavevector Q instead of the polar angle $\theta$. The momentum transfer wavevector is defined as the difference between the wavevectors of the incident and scattered light. The magnitude Q of Q in terms of the polar angle may be given by Eq. (29):

$$Q = 2n_m k_0 \sin\left(\frac{\theta}{2}\right) \quad \text{Eq. (29)}$$

The characteristic time for intensity fluctuation patterns to become uncorrelated in amplitude and phase between images, as required for validity of Eq. (13), is given by Eq. (30):

$$t_d = \frac{1}{DQ^2} \quad \text{Eq. (30)}$$

In Eq. (30), D represents the diffusion coefficient.

For Brownian motion of 1-micron radius spherical particles in water (viscosity=0.01 poise) at 300 Kelvin, $D=2.2\times 10^{-9}$ cm$^2$/sec. Eq. (30) may be used to provide an indication of the maximum exposure time for each intensity fluctuation image when Q corresponds to the largest scattering angles to be measured, which, in some implementations, may be limited to no more than $\pi/2$ radians.

Eq. (30) also may provide a minimum time between exposures when Q corresponds to the minimum scattering angle to be resolved. This minimum time can be estimated by setting Q equal to $\Delta q_x$ or $\Delta q_y$ in Eq. (30). Diffusion rates can be obtained with Eq. (30) by experimentally determining one or both of these limiting times by making a comparison of the results of analyzing different sequences of intensity fluctuation images where the exposure time and/or the time between exposures is varied.

In some implementations, the above calculations may be somewhat differently expressed as a calculation of a relationship between the intensity correlation and the amplitude correlation with respect to the near field scattering measurements. That is, the transmitted incident light field and the scattered light field may be treated as two components, and then the field amplitude correlation of the scattered field may be calculated from the measurements of the intensity fluctuations. The transmitted incident light field may include the effects of fixed sources of stray light.

In this type of analysis, and using capital letters for intensity values and lower case letters for corresponding amplitudes, an intensity that is resultant from a combination of two fields may be expressed as in Eq. (31):

$$I = |a+b|^2 \quad \text{Eq. (31)}$$

Eq. (31) may be re-written as Eq. (32):

$$I = A + B + 2Re(ab^*) \quad \text{Eq. (32)}$$

Then, the expected ensemble averaged and time averaged intensity may be shown as in Eqs. (33), (34), and (35), respectively:

$$\langle I \rangle = \langle |a+b|^2 \rangle \quad \text{Eq. (33)}$$

$$\overline{I} = \overline{|a+b|^2} \quad \text{Eq. (34)}$$

$$\langle \overline{I} \rangle = \langle \overline{|a+b|^2} \rangle \quad \text{Eq. (35)}$$

Using known relationships between moments of intensity of the sum of a speckle field (as the scattered field may be considered) and a constant field, the respective mean intensity contributions, A and <B>, to the speckle pattern resulting from the combination of a constant transmitted field with a speckle field from scattered light may be determined using Eqs. (36) and (37):

$$A = [2\langle I \rangle^2 - \langle I^2 \rangle]^{1/2} \quad \text{Eq. (36)}$$

$$\langle B \rangle = \langle I \rangle - [2\langle I \rangle^2 - \langle I^2 \rangle]^{1/2} \quad \text{Eq. (37)}$$

The result of Eq. (37) may be obtained from Eq. (32) using the fact that $A=|a|^2$ is constant, while b is a circular Gaussian random variable with zero mean. The averages indicated may be obtained, by example, from pixel-by-pixel averages of measured intensity and measured intensity squared over a sufficiently long sequence of images that have statistically independent realizations of the speckle field. The constant field may not be independent of position, but may be constant in time.

To obtain the best estimate of $\langle B \rangle$ and $A_{ij}$ for pixel i, j, the time average of the intensity $\overline{I}hd\,ij$ and squared intensity $\overline{I_{ij}^2}$ for all pixels, may be determined, and then the estimates of $\langle B_{ij} \rangle$ may be calculated from Eq. (39) using the time averages as estimates of the ensemble averages. Finally, if the scattered light is assumed to be statistically stationary, then the estimates $\langle B_{ij} \rangle$ of $\langle B \rangle$ may be averaged over all pixels. The resulting estimate of $\langle \overline{B} \rangle$ may then be used with Eq. (32) to recalculate the estimates of $A_{ij}$ from the per-pixel intensity time averages.

In order to obtain the mutual intensity of the speckle field, the spatial intensity correlation may be used, as shown in Eq. (38):

$$R_{(I-A)}(x_1, y_1; x_2, y_2) = \langle (I_1 - A_1)(I_2 - A_2) \rangle \quad \text{Eq. (38)}$$
$$= \langle [B_1 + 2\mathrm{Re}(a_1 b_1^*)][B_2 + 2\mathrm{Re}(a_2 b_2^*)] \rangle$$
$$= \langle B_1 B_2 \rangle + 2\langle B_1 \mathrm{Re}(a_2 b_2^*) + B_2 \mathrm{Re}(a_1 b_1^*) \rangle +$$
$$4\langle \mathrm{Re}(a_1 b_1^*) \mathrm{Re}(a_2 b_2^*) \rangle$$

The expectation value in the middle term of the last equality of Eq. (38) may be shown to be zero using, for example, an expression for a joint probability density function for intensity and phase.

If the fields are stationary, the intensity autocorrelation may be rewritten as a function of the difference vector ($\Delta x$, $\Delta y$)=($x_2-x_1$, $y_2-y_1$), and the first term may be written as the intensity autocorrelation of the speckle field, yielding Eq. (39):

$$R_{(I-A)}(x_1, y_1; x_2, y_2) = R_B(\Delta x, \Delta y) + 4\langle \mathrm{Re}(a_1 b_1^*) \mathrm{Re}(a_2 b_2^*) \rangle \quad \text{Eq. (39)}$$

A relation between the intensity autocorrelation and the amplitude autocorrelation, or mutual intensity $J_b(x_1, y_1; x_2, y_2) = \langle b_1 b_2 \rangle$ of a complex circular Gaussian speckle field that allows information about the field autocorrelation of the scattered light to be derived from the measurement of the intensity and its autocorrelation is shown in Eq. (40):

$$R_B(x_1, y_1; x_2, y_2) = \langle B \rangle \langle B_2 \rangle + |J_b(x_1, y_1; x_2, y_2)|^2 \quad \text{Eq. (40)}$$

Evaluating the expectation taken in the last term of Eq. (39) yields Eq. (41):

$$4\langle \mathrm{Re}(a_1 b_1^*) \mathrm{Re}(a_2 b_2^*) \rangle = \langle a_1 b_1^* a_2 b_2^* + a_1 b_1^* a_2^* b_2 + a_1^* b_1 a_2 b_2^* + \quad \text{Eq. (41)}$$
$$a_1^* b_1 a_2^* b_2 \rangle$$
$$= a_1 a_2 \langle b_1^* b_2^* \rangle + a_1 a_2^* \langle b_1^* b_2 \rangle + a_1^* a_2 \langle b_1 b_2^* \rangle +$$
$$a_1^* a_2^* \langle b_1 b_2 \rangle$$
$$= a_1 a_2^* \langle b_1^* b_2 \rangle + a_1^* a_2 \langle b_1 b_2^* \rangle$$

The averages in terms dropped within the development of Eq. (41) may be shown to have zero expectation. The two remaining terms can be written in terms of the mutual intensity $J_b$.

Then, substituting Eqs. (40) and (41) into Eq. (39) leads to Eqs. (42) and (43):

$$R_{\Delta I}(x_1, y_1; x_2, y_2) = \langle B \rangle^2 + |J_b(x_1, y_1; x_2, y_2)|^2 + 2\mathrm{Re}[a_1^* a_2 J_b(x_1, y_1; x_2, y_2)] \quad \text{Eq. (42)}$$

$$R_{\Delta I}(x_1, y_1; x_2, y_2) + A_1 A_2 - \langle B \rangle^2 = |a_1 a_2^* + J_b(x_1, y_1; x_2, y_2)|^2$$
$$[R_{\Delta I}(x_1, y_1; x_2, y_2) + A_1 A_2 - \langle B \rangle^2]^{1/2} = |a_1 a_2^* + J_b(x_1, y_1; x_2, y_2)| \quad \text{Eq. (43)}$$

In Eq. (42), the terms $R_{\Delta I}(x_1, y_1; x_2, y_2)$ and $\langle B \rangle^2$ represent terms that may be calculated from the measurements taken by the computer 230. The remaining two terms of the first line of Eq. (42), both written in terms of the mutual intensity $J_b$, represent terms referred to as the homodyne and the heterodyne components, respectively.

That is, the homodyne component $|J_b(x_1, y_1; x_2, y_2)|^2$ represents components of the scattered light resulting from scattering of light from the laser 214 or other light source 104, and, in particular, interference between such components. In contrast, the heterodyne component $2\mathrm{Re}[a_1^* a_2 J_b(x_1, x_2; y_1, y_2)]$ is related to interference between the transmitted light that is not scattered by the scattering medium 102 interfering with components of the scattered light.

The homodyne component may become small or negligible relative to the heterodyne component when, for example, a density of the scattering medium 102 is low, and/or in other situations in which an amount of scattered light is small relative to the transmitted light. Conversely, the heterodyne component may be removed, for example, either by a high density scattering medium 102 or by a beam stop or other physical mechanism for preventing the transmitted light from reaching the detector array, or by a high density of scattering material minimizing the transmission of light without scattering, i.e., the factors $a_1^* a_2$ each approach zero.

Using the above Eqs. (31)-(42), perhaps in conjunction with some or all of the Eqs. (1)-(30) above, the spatial correlation function of the electric field at the detector array may be determined from the intensity variations measured there. For example, the expressions $\langle (I_1-A_1)(I_2-A_2) \rangle$ in Eq. (38) represent the intensity variation at two pixels in a given image. Thus, a correlation of the intensity variation as a function of positions of a pair of pixels $[x_1, y_1; x_2, y_2]$ may be determined without requiring an assumption that the stray light component of the total scattered light is statistically spatially stationary.

As a result, with respect to Eq. (42), the final line of Eq. (42) may be solved for the spatial correlation function of the electric field by, for example, suitable averaging or estimation techniques to eliminate measurement uncertainties and/or unknown phase factors in the stray light terms. For example a maximum likelihood estimate may be made of the combination of electric field autocorrelation $J_b(x_1, y_1; x_2, y_2)$ and constant factors $a_1^* a_2$ that produced the sequence of images, taking advantage of the fact that Jb may be dependent on its two position arguments $(x_1, y_1)$ and $(x_2, y_2)$ only through the difference $(\Delta x, \Delta y)$.

Figure 4:
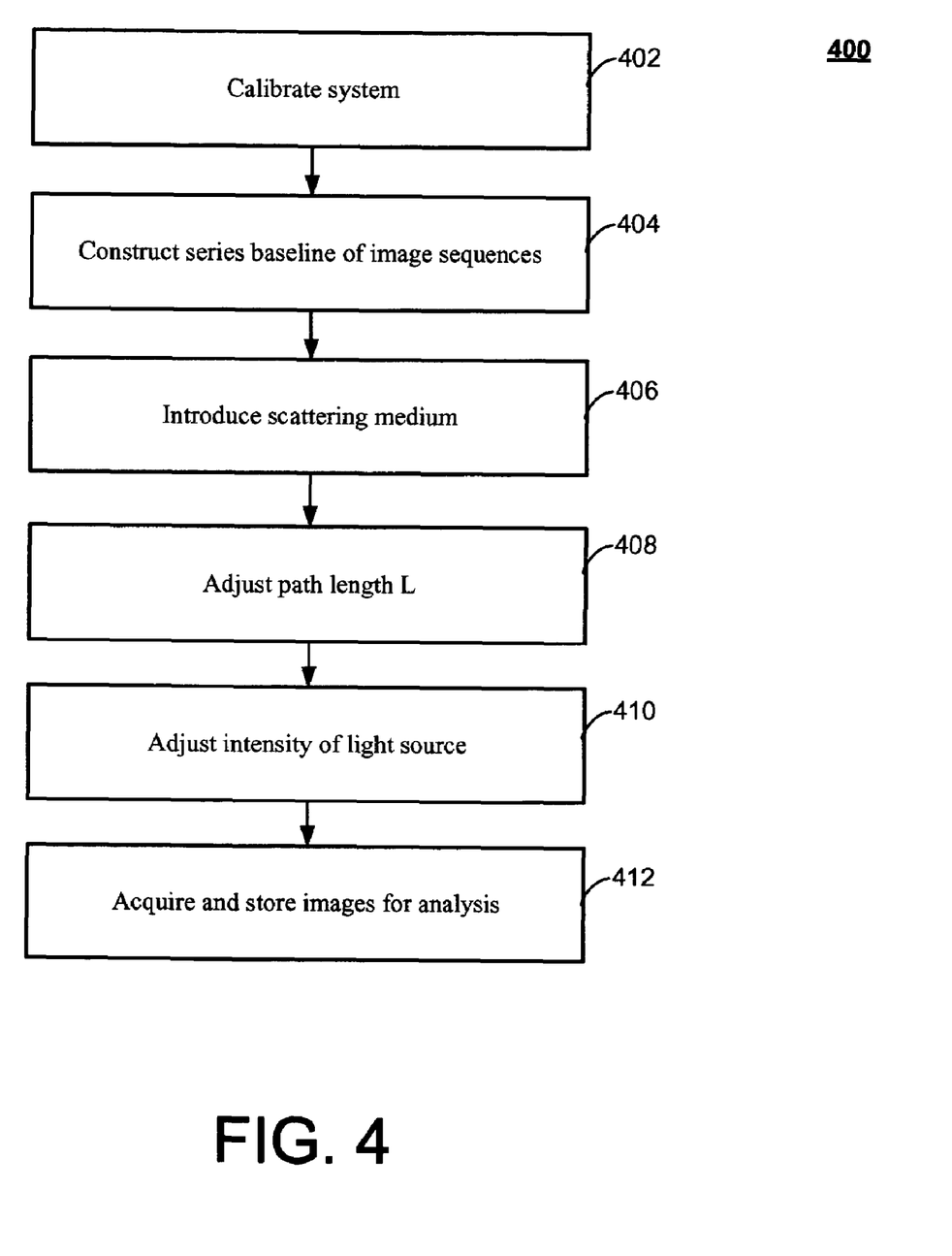
FIG. 4 is a flowchart illustrating examples of operations of the systems of FIGS. 1 or 2.

FIG. 4 is a flowchart illustrating examples of operations of the systems of FIGS. 1 or 2, using selected ones of the Eqs. (1)-(42). Using the example of FIG. 2, calibration of the system 200 may be implemented and automated through the use of the computer 230 (402). For example, making a measurement with the system 200 with no scattering medium being present (or with a blank medium) and allowing storage of the resulting intensity distribution will allow the user to have a comparative system baseline.

Periodically, the user will be able to acquire an intensity distribution with no scattering medium, for comparison with the system baseline that has previously been stored. This comparison may generally require that these two measurements be performed with the same system settings. Finding the difference between these two distributions and analyzing the resultant signal may allow the user to monitor the status of the system and facilitate detection of any changes that may possibly alter the ability of the system to perform an accurate measurement.

Before each series of measurements, it would be desirable for the user to construct a series run baseline (404) to use for comparison with the previous baseline(s) and/or subsequent experimental measurements. The new baseline may be used to aid in the analysis of the data and to allow a check for any discrepancies within the system 200. At the discretion of the user during routine use, this series baseline comparison may be performed when the user feels a check is required or suspects the equipment is operating in a faulty manner.

If certain changes have been made to the optical setup, such as, for example, changing certain optical components, adjusting any optical settings, or changing any beam diameters, a new system baseline measurement should be performed to allow the user to determine the status of the system. If any discrepancies are noted, the necessary adjustments may be made.

During normal use, a sample is introduced into the volume between the window 110 and the assembly 116 (406). The path length L is adjusted as desired (408), and the intensity of the laser 214 is then adjusted (410) to provide adequate intensity for the digital imaging system 228, without causing saturation.

The computer 230 then commands acquisition of a sequence of images at an exposure time $t_1$ and a time between exposures $t_2$, and stores the sequence for analysis (412). Details of the settings, including exposure time, and time between exposure, depend on the particular set of measurements desired. The following discussion includes examples for determining settings and measurements that may be needed for a given application.

As should be understood from FIG. 1, the path length L, the source light parameters, and the image acquisition settings all may be controlled by the corresponding modules of the imaging controller 108, as described therein. In FIG. 2, such modules may be included within, and/or implemented by, the computer 230, and/or by other, separate hardware or software components.

Figure 5:
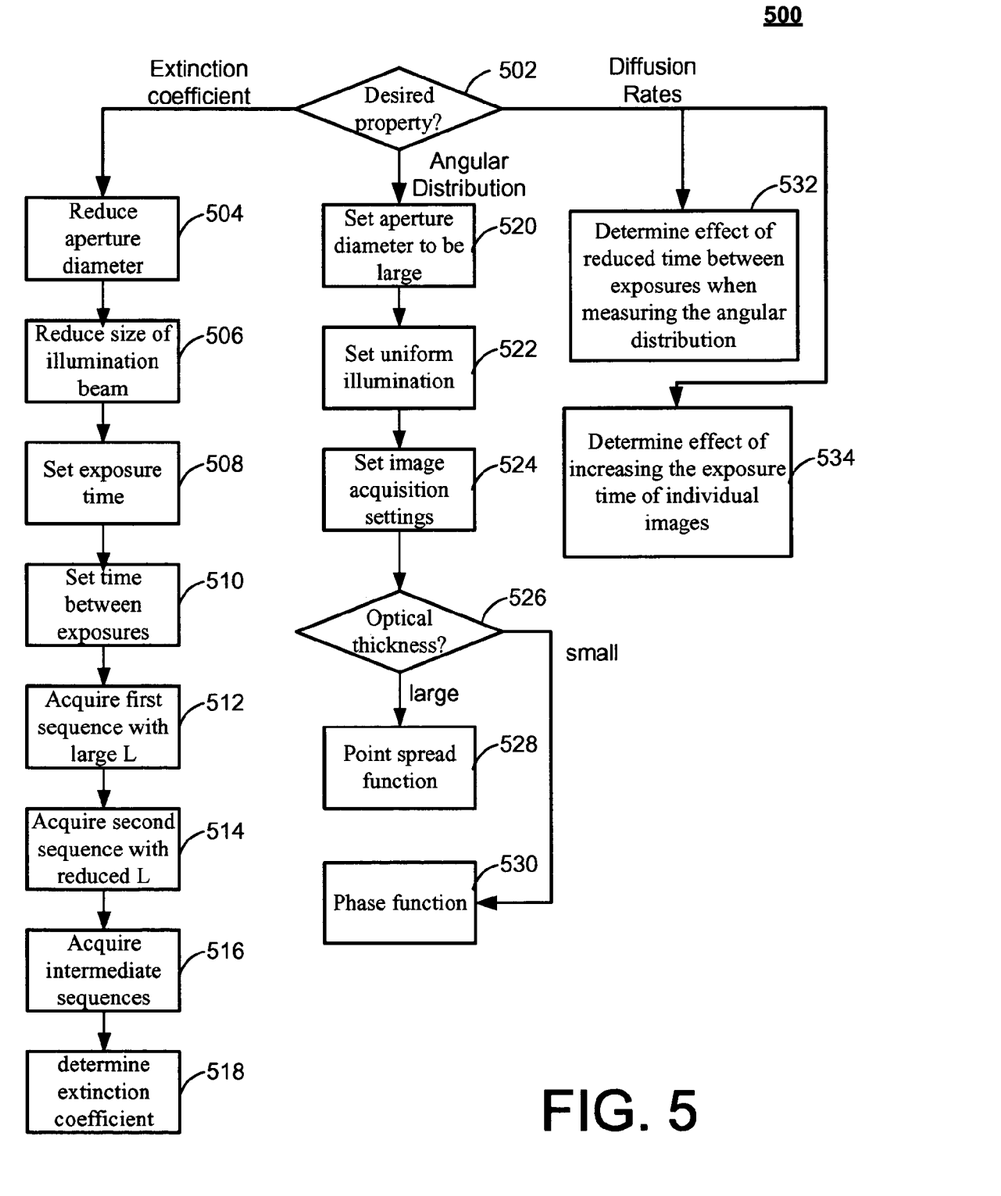
FIG. 5 is a flowchart illustrating techniques for determining properties of a scattering medium.

FIG. 5 is a flowchart illustrating techniques for determining properties of the scattering medium 102. For example, such techniques may be employed as part of the path length adjustments (408), source light adjustments (410), or the acquiring, storing, and analyzing of the intensity image data itself (412), depending on, for example, which property of the scattering medium is to be determined (502).

For example, to measure an extinction coefficient $\xi$, the diameter of the aperture 112 may be reduced to limit the scattered light recorded in the image sequences (504). Also, the size of the illumination beam from the spatial filter assembly 222 may be proportionally reduced by adjusting the zoom setting to increase the intensity of illumination (506).

The exposure time $t_1$ may be set so as to be short compared with the minimum diffusion time expected (508), and the time between exposures $t_2$ may be set to be long compared with the longest diffusion time expected (510). In some implementations, image sequences of approximately 100 images are used.

A first sequence may be determined using a desired concentration of the scattering medium 102, with the path length L set to a suitably large value, e.g., its maximum travel (512). A suitably large path length L may be determined to be one that achieves an optical thickness (the product $\xi L$ in the exponent of Eq. (19)) satisfactorily large compared with the uncertainties of the measurements. In some implementations, the optical thickness may not be so large that the measurement breaks down because of excessive multiply-scattered light.

A second series may be acquired with a significantly smaller optical thickness (514), either by, for example, reducing the path length L, or by using a blank sample in place of the scattering material. Additional sequences at intermediate values of the path length L (516) may allow determination of the extinction coefficient from a straight-line fit of the logarithm of the transmitted light A(L) plotted against the path length L (518). Deviations from a straight line at large values of L may indicate breakdown of the measurement because of excessive multiply-scattered light. Results at those large values of L may be discarded.

For a measurement of the angular distribution of scattered light, the aperture a1 may be set to a relatively large diameter (520), such that any particles away from the optical axis capable of scattering light in the direction of the region 120 may be illuminated by the incident beam. Also, the spatial filter assembly 222 may be set so that the illumination is uniform over the aperture 112 (522). The exposure time, time between exposures, and number of images needed are determined in the same way as for the measurement of an extinction coefficient (524). Sequences of more than 100 exposures may reduce the variance of the measurements. Alternatively, if lower angular resolution is acceptable, the variance also may be reduced by smoothing the results.

Depending on the optical thickness chosen for the measurement (526), a measurement of the angular distribution of scattered light for a sample may allow determination of the point-spread function (528) or phase function (530) of the sample. To obtain the phase function, the optical thickness must be small compared with 1. A phase function measurement may thus utilize a small setting for the path length L, a dilute sample, or both. A proper normalization of the angular distribution obtained from the measurement may yield the phase function.

More generally, the angular distribution measurement is the point-spread function less the distribution of the transmitted light, which is known from, for example, the illumination system characteristics and the results of Eq. (15). The point-spread function is dependent on the scattering material and the optical thickness. Therefore, a length of the path length L may be chosen that results in the optical thickness representative of conditions for which the point-spread function is desired.

Diffusion rates may be obtained by determining the effect of reducing the time between exposures when measuring the angular distribution of scattered light (532), or of increasing the exposure time of the individual images (534). In the first case, one approach is to perform the angular distribution measurement with additional exposures made by decreasing the time between exposures and increasing the number of exposures to maintain the same overall acquisition time. The results obtained from subsets of exposures with large and smaller times between exposures may then be compared.

For example, if the time between exposures is reduced by a factor of 5, 500 exposures may be acquired instead of 100. A subset comprising every fifth exposure is used for 1 calculation of the angular distribution and compared with the results from a subset comprising the first 100 exposures. The spatial frequency at which the measurement based on the second subset deviates significantly from the measurement based on the first indicates the diffusion rate. Other settings will be similar to the settings used for a phase function determination. Suitable calibration may allow diffusion rate measurements for samples of higher optical thickness.

The effects of increasing the exposure time of the individual images (540) may be evaluated with two or more recorded sequences. In one sequence, the settings should be those appropriate for sequences used in measuring angular distribution of scattered light. In the rest of the sequences, the settings should be the same except that the exposure time should be increased from one sequence to the next, so that there are two or more sequences, each with a fixed exposure time different from that of the others. The analysis technique for determining the diffusion rate is similar to that for analyzing the effect of shorter time between exposures described above. In this case, the deviation between measurements can be expected to start at higher spatial frequencies for small increases in exposure time, and progress to lower spatial frequencies as the exposure time increases further. In the previous case, the deviations start at lower spatial frequencies and appear at higher and higher spatial frequencies, as the time between exposures is reduced.

Data useful for retention as baseline or calibration records include measurements as described in the above examples for a suitable standard sample, such as a suspension of known materials, particle size, shape, and concentration. Such reference standards are available from, for example, suppliers that use a repeatable synthesis technique. Polystyrene microspheres suspensions in water of a specified, uniform size are an example of an available reference standard material. In addition, the time-average images may be retained along with the supporting data, including settings, needed for the stray light calculations in Eqs. (16), (18), and (22).

This information may be useful for monitoring changes in the stray light and/or in establishing the extent to which the stray light signal is repeatable. For example, the stray light effects may be repeatable over a series of measurements where certain settings are unchanged. Combining these retained records may then improve the accuracy of the stray light corrections or reduce the number of images required for a sequence.

These features may be applicable for at least two of the examples above: extinction measurements made at fixed settings by varying the particle concentration of the sample, and diffusion rate measurements using sequences where the setting change is only to the exposure time of individual images. Additional gains are possible if these records establish that stray light effects are repeatable if the same settings are used as for previous measurements. For example, the stray light results may be the same whenever the setting of the path length L is returned to a previously used value.

The techniques of FIGS. 3-5 may be implemented in other variations of the systems of FIG. 1 and/or 2. For example, in some other implementations, the microscope objective 206 may be fitted with a mask in the form of a straight-edge mask located in the back focal plane of the microscope objective 206. Such a mask may be used, for example, by adjusting the position of the edge with a micrometer to bisect the back focal plane at the center of the focused transmitted beam on the optic axis of the microscope objective 206. The described analysis of the angular distribution of scattered light from the intensity fluctuation measurements may be modified to account for the elimination of negative spatial frequencies in one direction. Such an alternative allows the distance Z from the scattering sample to the region 120 to be reduced without complicating the calibration of the measurement, and allows use of scattering media having relatively large optical thicknesses than may otherwise be available.

In an alternative arrangement, illumination from the opposite side of the scattering medium 102 may be used to measure angular distribution of backscattered light about the direction of retroreflection (180 degrees). For example, the laser 214, spatial filter assembly 222, and intensity monitor 216 with beamsplitter 218 may be arranged such that the beamsplitter 218 is placed between the microscope objective 206 and the lens 226 to direct one beam axially into the back of the microscope objective 206.

In such implementations, the aperture 112 may not be needed. Instead, for example, a focusing system may be placed between the spatial filter assembly 222 and the beamsplitter 218 so that the illumination forms a cone of light with its vertex in the back focal plane of the microscope objective 206. After passing the back focal plane, the cone of light expands again and is then collimated by the microscope objective 206.

The focusing system may be designed to compensate for aberrations caused by the beamsplitter 218 and the microscope objective 206 when used for collimating a source in the back focal plane instead of in the front focal plane discussed with respect to FIGS. 1 and 2. The focusing system may have an entrance pupil large enough to make the collimated light beam diameter as large as possible upon exiting the end of the microscope objective 206 in the direction of the front focal plane. The collimated light beam diameter may match the size of the aperture 112 at the end of the microscope objective 206, and a long working distance microscope objective should be used. This and similar implementations also may be used, for example, to analyze light from randomly rough surfaces of solids.

A maximum thickness of fluid samples may be smaller than the working distance of the microscope objective 206 when the maximum angular range of backscatter from the retroreflection direction is to be measured. The spatial filter assembly 222 may have a fixed focal length collimating lens instead of a zoom lens. The size of the expanded beam may be sufficient to provide uniform illumination within the entrance pupil of the focusing system. This arrangement can be combined with the use of a mask, as described in implementations, above.

Dependence of scattering on polarization may be obtained with the addition of polarizing optics and a second imaging system. For example, a polarizing beamsplitter may be placed between the microscope objective 206 and the positive lens 226. The second output of the beamsplitter 218 illuminates another positive lens and digital imaging system. A polarizer in front of the aperture 112 polarizes the light and illuminates the scattering medium 102.

In another implementation, the window 110 may be made moveable to adjust the path length L. In this case, the window 110 may be the bottom of a vessel for containing the scattering medium 102. The vessel may be set on top of the stage of a digital microscope, and the collimated laser illumination may be introduced from beneath the stage, directed upwards by a mirror, for example.

The assembly 116 may be a simple canister forming the shield 202, with the extension window 204 at the bottom and the mask 118 inside. The assembly 116 may be made to fit over a microscope objective and fixed in place, so that the bellows 212 or translation stage 210 is not required. The assembly 116 and the vessel with the window 110 may be attachments for a digital microscope that has a means for directing the illumination upwards from under the stage through the window 110.

The digital microscope in these implementations may substitute for the combination of microscope objective 206, lens 226, and digital imaging system 228. Other components may be arranged as described above. In these implementations, the components of a digital imaging system may be implemented as a conversion for a digital microscope that can be attached and removed again, allowing the digital microscope to be used for multiple purposes.

In another implementation, reflecting surfaces parallel to the collimated laser illumination may be used to confine the scattered light, from the window 110 to the near-field region 120. These surfaces would form a prism with a cross section matching the area of the region 120 that images on the two-dimensional detector array 232. Within the scattering medium 102, between the window 110 and the extension window 204, a reflecting coating may be applied. From the extension window 204, the reflecting surfaces may be used as an interface between a glass prism and air, and the mechanism of reflection may be total internal reflection. In this implementation, the outer shield 202 of the assembly 112 may not be required. These implementations may allow a smaller illuminating beam to be used, resulting in high light efficiency, and reducing a size of the spatial filter assembly 222.

Imaging systems as described herein allow characterization of various scattering properties of suspensions of small particles within a scattering medium. These properties may include, as in the examples above, the extinction coefficient, the effect on scattering of particle diffusion rates in the medium (and from the scattered intensity distribution as a function of angle), the volume scattering function, and/or the point-spread function versus optical thickness of the sample.

The imaging systems described herein, and related implementations, thus provide advantages including the ability to obtain stray light information (i.e., stray light due to imperfections or surface contamination of components of the optical train) directly from the sequence of image data made with the sample of scattering material to be measured, so that separate measurements of these factors may not be required. Other advantages may include insensitivity to nonuniformity in the response of the detector array, good angular resolution, and flexibility in the positioning of the region 120 where the measurements are made.

In addition, such imaging systems allow the combined use of intensity fluctuations resulting from interference between different components of the scattered light and fluctuations resulting from the interference of components of the scattered light with transmitted light. As a result, minimal system elements may be used, e.g., a beam stop in the back focal plane of the microscopic objective may not be required. Also, the optical thickness of the scattering medium need not be limited to values smaller than one scattering mean-free path length. Rather, measurements can be made with samples at higher concentrations of scattering particles, longer path lengths, or both, resulting in significantly greater optical thickness. Specifically, for example, scattering extinction coefficients and point-spread functions can be obtained for samples of optical thickness greater than 1.

Further advantages include the ability to adjust the path length L within the scattering medium in order to make measurements at a desired optical thickness, or at more than one value of optical thickness without changing the sample concentration. Also, optical thickness may be measured, along with particle diffusion times. Further, when the positive lens 226 is a part of the sensor assembly 116, the resulting imaging system may allow flexibility in choosing the separation of the lens 236 and the assembly 116 from the microscope objective 206.

As a result, the described imaging systems and variations thereof may be used to characterize optical properties of scattering media. Optical characteristics may be discovered that could be exploited for detection of specific types of particles, such as, for example, biological agents. Also, types of particles may be distinguished from other particles, e.g., background particulates. Additional examples of applications include monitoring of optical properties of scattering media. In ocean optics, for example, the local point-spread function could be monitored in aid of improving imaging through turbid water.

A number of implementations have been described. Nevertheless, it will be understood that various modifications may be made. Accordingly, other implementations are within the scope of the following claims.

What is claimed is:

1. A system comprising:
    a light source for directing light towards a scattering medium that has a path length therethrough;
    a digital imaging system for receiving the light transmitted through the scattering medium substantially without being scattered, and for receiving interference effects among plurality of scattered light components that pass through the scattering medium after being scattered thereby, and further providing image intensity information that results from interference among the components; and
    an imaging controller for determining a property of the scattering medium, based on spatial correlations related to the image intensity information, and further for adjusting the path length.

2. The system of claim 1 wherein the plurality of scattered light components includes at least one of singly-scattered, doubly-scattered, or multiply-scattered light components.

3. The system of claim 1 wherein the digital imaging system is operable to determine interference effects among the transmitted light and the plurality of scattered light components.

4. The system of claim 1 wherein the image intensity information includes at least a sequence of images, and the spatial correlations are determined between selected points within each image of the sequence.

5. The system of claim 1 wherein the imaging controller is operable to determine the property by accounting for effects of stray light that is scattered by portions of the system other than the scattering medium, with respect to the spatial correlations.

6. The system of claim 1 further comprising:
    an assembly containing a near-field region at which light having passed through the scattering medium is focused for imaging by the digital imaging system; and
    a window placed between the light source and the scattering medium,
    wherein the assembly and the window are movable relative to one another so as to vary the path length of light through the scattering medium by the imaging controller.

7. The system of claim 6 wherein the digital imaging system includes a digital microscope, and wherein the assembly includes a vessel that is operable to attach to the digital microscope.

8. The system of claim 7 wherein the light from the light source is coherent, collimated light.

9. The system of claim 8 comprising reflecting surfaces that are parallel to the collimated light and operable to confine the scattered light between the window and the near-field region.

10. The system of claim 6 comprising a microscopic objective within the assembly, wherein a focal plane of the microscopic objective coincides with the near-field region.

11. The system of claim 10 wherein the microscopic objective includes an oil-immersion-type objective with an infinity conjugate distance.

12. The system of claim 6 comprising an aperture having a diameter and defined between the window and the light source.

13. The system of claim 12 wherein the imaging controller is operable to modify the path length, the diameter, properties of the light source, or any combination thereof, and to determine the property of the scattering medium based thereon.

14. The system of claim 13 wherein the property includes an extinction coefficient of the scattering medium, and wherein the imaging controller is operable to determine the extinction coefficient by acquiring the image intensity information as a plurality of sequences of images, each sequence having a different path length L.

15. The system of claim 1 wherein the property includes an angular distribution of the scattered light.

16. The system of claim 15 wherein the imaging controller is operable to determine a point spread function associated with the scattering medium.

17. The system of claim 1 wherein the scattering medium includes a plurality of suspended particles.

18. The system of claim 16 wherein the property includes a diffusion rate of the suspended particles.

19. The system of claim 18 wherein the imaging controller is operable to determine the diffusion rate based on a time between exposures of a sequence of images used to determine the image intensity information, or based on a time of exposure of individual images within the sequence.

20. The system of claim 1 wherein the light source directs the light to a side of the scattering medium that faces the digital imaging system.

21. The system of claim 1 comprising:
a beamsplitter for dividing the light from the light source into at least two beams;
polarizing optical components for receiving and polarizing at least one of the two beams; and
a secondary digital imaging system for obtaining secondary image intensity information related to the polarized one of the two beams,
wherein the imaging controller is operable to determine a dependence of scattering within the scattering medium, based on the secondary image intensity information.

22. A method comprising:
receiving a sequence of images that are formed as a result of source light that has traveled through a scattering medium having particles suspended therein, the images containing image intensity information for each of the images;
determining spatial correlations between intensities of at least two points in each image;
accounting for effects of transmitted light that is passed through the scattering medium substantially without scattering, based on the spatial correlations;
analyzing interference effects of interference among components of scattered light that is scattered by the particles, based on the spatial correlations; and
determining a property of the scattering medium, based on the accounting for the effects of transmitted light, the analyzing of the interference effects, and on the spatial correlations, wherein receiving the sequence of images comprises adjusting a path length of the scattering medium.

23. The method of claim 22 wherein determining the property of the scattering medium comprises accounting for stray light effects related to stray light that is scattered by components other than the scattering medium.

24. The method of claim 22 wherein receiving the sequence of images comprises:
receiving the transmitted light and the scattered light at a near-field region at which light having passed through the scattering medium is focused for imaging.

25. The method of claim 22 wherein receiving the sequence of images comprises adjusting a diameter of an aperture between the window and an origin of the source light, through which the source light passes.

26. The method of claim 25 wherein determining the property of the scattering medium comprises:
modifying the path length, the diameter, properties of the light source, or any combination thereof; and
determining the property of the scattering medium based thereon.

27. The method of claim 22 wherein determining the property of the scattering medium comprises determining an extinction coefficient of the scattering medium.

28. The method of claim 22 wherein determining the property of the scattering medium comprises determining an angular distribution of the scattered light.

29. The method of claim 28 wherein determining the angular distribution of the scattered light comprises determining a point spread function associated with the scattering medium.

30. The method of claim 28 wherein determining the angular distribution of the scattered light comprises determining a phase function associated with the scattering medium.

31. The method of claim 22 wherein determining the property of the scattering medium comprises determining a diffusion rate of the suspended particles.

32. An imaging controller comprising:
an imaging system controller for determining imaging characteristics of a digital imaging system at which a detecting system detects both scattered light and transmitted light that both pass through the scattering medium, the scattered and transmitted light originating from a light source, the scattering medium having a path length through which the scattered and transmitted light pass; and
an image analyzer that is operable to:
receive image intensity data from the digital imaging system,
determine spatial correlations that are associated with the image intensity data, based on interference between components of the scattered light, and further based on the transmitted light,
determine a property of the scattering medium, based on the spatial correlations, and
adjust the path length of the scattering medium.

33. The imaging controller of claim 32 wherein the image analyzer comprises a path length adjuster that adjusts the path length of the scattering medium.

34. The imaging controller of claim 33 wherein the image analyzer comprises a light source adjuster that is operable to adjust parameters of the light source.

35. The imaging controller of claim 34 wherein the image analyzer comprises a diameter adjuster that is operable to adjust a diameter of an aperture through which the source light passes before entering the scattering medium.

36. The imaging controller of claim 32, wherein the property includes at least one of an extinction coefficient, an angular distribution of the scattered light, and a diffusion rate of particles suspended within the scattering medium.

37. The imaging controller of claim 32 wherein the image analyzer is operable to account for an effect of stray light received by the digital imaging system that has been scattered by components other than the scattering medium.

* * * * *